US010993666B2

(12) United States Patent
Govari et al.

(10) Patent No.: US 10,993,666 B2
(45) Date of Patent: *May 4, 2021

(54) MIDDLE POINT ZERO REFERENCE

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 90 days.

This patent is subject to a terminal disclaimer.

(21) Appl. No.: 16/432,497

(22) Filed: Jun. 5, 2019

(65) Prior Publication Data

US 2019/0282171 A1    Sep. 19, 2019

Related U.S. Application Data

(63) Continuation of application No. 15/723,419, filed on Oct. 3, 2017, now Pat. No. 10,321,876.

(51) Int. Cl.
*A61B 5/00* (2006.01)
*A61B 5/283* (2021.01)
(Continued)

(52) U.S. Cl.
CPC ............ *A61B 5/6852* (2013.01); *A61B 5/283* (2021.01); *A61B 5/287* (2021.01); *A61B 5/316* (2021.01); *A61B 5/339* (2021.01); *A61B 5/349* (2021.01); *A61B 5/361* (2021.01); *A61B 5/7203* (2013.01); *A61N 1/365* (2013.01)

(58) Field of Classification Search
CPC ..... A61B 5/6852; A61B 5/7203; A61B 5/042; A61B 5/046; A61B 5/04012; A61B 5/0422; A61B 5/044; A61B 5/0452; A61B 1/365; A61B 5/0402; A61B 5/04085; A61B 18/12; A61B 18/1492; A61B 2018/00351;
(Continued)

(56) References Cited

U.S. PATENT DOCUMENTS 5,697,377 A   12/1997   Wittkampf
6,023,638 A    2/2000   Swanson
(Continued)

FOREIGN PATENT DOCUMENTS

EP    1169974 A1    1/2002

OTHER PUBLICATIONS

Extended European Search Report dated Feb. 20, 2019 for the European Patent Application No. 18198266.1.

*Primary Examiner* — Scott M. Getzow

(57) ABSTRACT

A cardiac electrophysiology system including a means for identifying the source of an arrhythmia in the heart is disclosed. The disclosed system may be an electrocardiograph device and may generate an enhanced electrocardiogram (EKG) of a cardiac structure. The disclosed system may include a disclosed catheter inserted into a chamber of the cardiac structure. The disclosed catheter may include electrodes configured to measure an analog electrical signal of the electrical activity of the cardiac structure over time, and a transformer configured to remove a direct current (DC) offset of the analog electrical signal to generate an analog electrical signal centered at 0 volts (V), which may be sampled by an analog-to-digital converter (ADC) and gain adjusted to a maximum resolution of the ADC to produce an enhanced digital electrocardiogram (EKG) signal.

20 Claims, 3 Drawing Sheets

(51) Int. Cl.
*A61B 5/287* (2021.01)
*A61B 5/316* (2021.01)
*A61B 5/339* (2021.01)
*A61B 5/349* (2021.01)
*A61B 5/361* (2021.01)
*A61N 1/365* (2006.01)

(58) Field of Classification Search
CPC ........... A61B 2018/00595; A61B 5/0404–044; A61B 5/061; A61B 5/72–7232
See application file for complete search history.

(56) References Cited

U.S. PATENT DOCUMENTS

| 6,391,024 | B1 | 5/2002 | Sun et al. |
| 2007/0073179 | A1 | 3/2007 | Afonso et al. |
| 2017/0065198 | A1 | 3/2017 | Ruppersberg |

MIDDLE POINT ZERO REFERENCE

CROSS REFERENCE TO RELATED APPLICATION(S)

This application is a continuation of U.S. patent application Ser. No. 15/723,419, filed Oct. 3, 2017, which is/are incorporated by reference as if fully set forth.

SUMMARY

A cardiac electrophysiology system including a means for identifying the source of an arrhythmia in the heart is disclosed. The disclosed system may be an electrocardiograph device and may generate an enhanced electrocardiogram (EKG) of a cardiac structure. The disclosed system may include a disclosed catheter inserted into a chamber of the cardiac structure. The disclosed catheter may include electrodes configured to measure an analog electrical signal of the electrical activity of the cardiac structure over time, and a transformer configured to remove a direct current (DC) offset of the analog electrical signal to generate an analog electrical signal centered at 0 volts (V), which may be sampled by an analog-to-digital converter (ADC) and gain adjusted to a maximum resolution of the ADC to produce an enhanced digital electrocardiogram (EKG) signal.

DETAILED DESCRIPTION OF THE EMBODIMENTS

Figure 1:
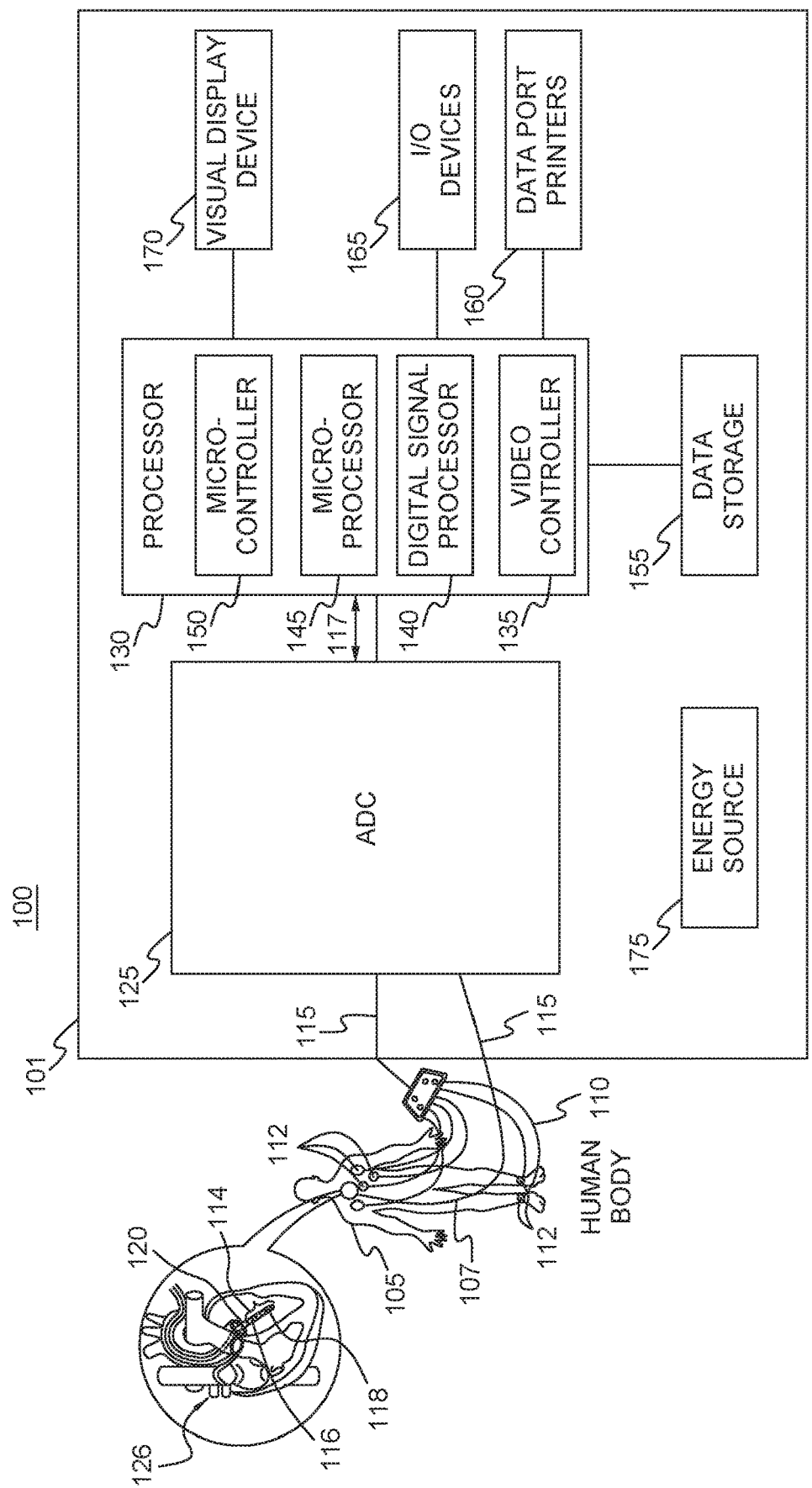
FIG. 1 is a schematic diagram of an example electrocardiograph device 100, in accordance with the disclosures herein.

Electrocardiography is a type of cardiology test that measures and records the electrical activity of the heart over a period of time using electrodes placed on the skin and/or inside the heart using a catheter. These electrodes detect the small electrical changes that arise from the heart muscle's electro-physiologic pattern of depolarizing during each heartbeat and thus can be used to detect abnormal cardiac conditions, such as myocardial infarction, pulmonary embolism, structural heart disease (e.g., cardiac murmur), or cardiac arrhythmia. Electrocardiography may be performed by an electrocardiograph machine and the resulting testing produces an electrocardiogram (abbreviated equivalently as EKG or ECG) showing the electrical signals in the heart, typically as graph of the voltage of the heart's electrical activity over time.

An example electrocardiograph system may include twelve leads and ten electrodes placed on the patient's limbs and on the surface of the chest. The overall magnitude of the electrical potential of the heart is measured from the twelve leads, each corresponding to a different measurement angle, and is recorded over a period of time. Electrocardiography performed with intracardiac electrodes, that are for example mounted on a catheter placed inside a chamber of the heart, produce and EKG referred to as an intracardiac electrocardiogram (ICEG), and may be utilized in combination with, or in the alternative to, the conventional twelve leads placed on the exterior of the patient. In order to measure heart muscle electrical activity, the EKG electrodes have to be able to detect very small changes in potential energy on the patient's skin or heart tissue. For example, the electrical changes may be detected by EKG electrodes as cardiac electrical signals measuring on the order of 1 millivolt (mV) or less. An ICEG may be able to capture electrical morphologies that may not be detected on an EKG using surface electrodes on the body surface only, or at least with more accuracy in certain cases.

During each heartbeat, a healthy heart has an orderly progression of depolarization. This orderly pattern of depolarization gives rise to the characteristic EKG tracing. To the trained clinician, the morphology of the EKG signal conveys a large amount of information about the structure of the heart and the function of its electrical conduction system. Among other things, an EKG can be used to measure the rate and rhythm of heartbeats, the size and position of the heart chambers, the presence of any damage to the muscle cells or conduction system of the heart, the effects of cardiac drugs, and the function of implanted pacemakers. Interpretation of the EKG is fundamentally about understanding the electrical conduction system of the heart. Normal conduction starts and propagates in a predictable pattern, and deviation from this pattern can be a normal variation or be pathological.

While EKGs produced by existing electrocardiograph systems are widely used in diagnosing and monitoring cardiac conditions, they have some known limitations. For example, an arrhythmia is a rhythm defect in the heart in which the heart beats irregularly, too fast, or too slow. Initial detection of a cardiac arrhythmia may be possible by the simplest of means, such as auscultation of the heartbeat or feeling for peripheral pulses, however more advanced testing is needed to diagnose the specific arrhythmia, which typically involves miniscule electrical signals that can only be detected when a high degree of accuracy is used. A conventional ICEG, employing intracardiac electrodes, may provide specific diagnostic testing for assessment of arrhythmias, but in many cases may not be an accurate way to detect the specific source of the arrhythmia in the heart tissue, as explained below.

In a conventional intracardiac electrocardiograph system, an EKG electrode in contact with the skin and/or cardiac tissue measures heart signal current flowing into the electrode as a positive charge, and heart signal current flowing away from the electrode as a negative charge, to produce a voltage reading of the heart's electrical signals over time. A goal of an electrocardiograph system is to minimize the artifacts and maximize the accuracy of the EKG signal in order to provide reliable information to the physician.

Impedance (i.e., the opposition to the electrical current) due to the patient's internal geometry can be problematic for the accuracy of an EKG by distorting the accuracy of voltage readings provided at an EKG electrode. As a result, it may be difficult to localize the source of the arrhythmia in the heart in the presence of the impedance caused by the surrounding body. For example, various body types such as large bones, high muscle mass or high obesity, may have different distortion effects on how a particular electrical signal from the heart is read by the EKG electrodes.

The disclosed electrocardiograph system and method improves the accuracy of EKGs for purposes of identifying the source of the arrhythmia and other conditions in the heart tissue by mitigating the distortion effects of the inherent impedance in the cardiac structure. Instead of using the heart's voltage as a reference voltage, a transformer (e.g., mounted on the catheter) that emits a low electric charge is placed inside the heart to create voltage signals recognized by the EKG electrodes to remove the voltage bias. For example, the electric charge emitted by the transformer may be on the order of several microvolts (μV) (e.g., in the range of 1-100 μV, or other example ranges). Thus, the transformer serves to find and isolate the control point, which is the area of maximum sensitivity where there is maximum change per unit of voltage due to the cardiac electrical activity.

Thus, according to the disclosed electrocardiograph system and method, the EKG electrodes are set together at the same middle point zero reference point and therefore measure cardiac electrical signals based on the charge emitted by the transformer inside the heart. Creating this single middle point zero reference inside the heart removes distortions due to impedance (e.g., caused by the geometry of the patient's internal body structure).

The catheter comprising the transformer and EKG electrodes may be moved around in the heart (e.g., by the physician physically moving the catheter via a handle) while emitting a small electric charge to stimulate the portion of the heart tissue causing the arrhythmia. For example, the electric charge emitted for stimulating cardiac tissue may be on the order of several millivolts (mV) (e.g., in the range of 1-100 mV, or other example ranges). The specific location of an arrhythmia may be located by the catheter because the muscle tissue causing the arrhythmia will respond, as atrial fibrillations, to the catheter so that the physician can isolate the arrhythmia on the EKG. Once the specific location of the arrhythmia in the heart is identified with the catheter, the EKG electrodes can take measurements of the isolated signals from the arrhythmia. The resulting EKG can be used as a more accurate tool to identify the source of an arrhythmia in the heart and to study the isolated heart tissue causing an arrhythmia.

FIG. 1 is a schematic diagram of an example electrocardiograph device 100, in accordance with the disclosures herein. The electrocardiograph device 100 may include, but is not limited to include, any of the following components: console system 101; intracardiac leads 107 connected to a catheter 120 with distal end 114 inserted into the heart 126 of the patient 105; non-contact electrodes 116 located at the distal end 114 of catheter 120; transformer 118 located at the distal end 114 of catheter 120; and leads 110 connected to electrodes 112 positioned in various locations on the skin of the patient 105. The console system 101 may include, but is not limited to include, any of the following components: analog-to-digital converter (ADC or A/D converter) 125; processor 130; data storage 155; data port printers 160; input/output (I/O) devices 165; visual display device 170; and/or energy source device 175. The processor 130 may include, but is not limited to include, any one or more of the following components: video controller 135; digital signal processor (DSP) 140; microprocessor 145; and/or microcontroller 150.

The catheter 120, leads 107 and 110, electrodes 112 and 116, transformer 118, and/or other components not shown (e.g., additional catheters, sensors, etc.) of the electrocardiograph device 100 may be used directly on, in, and/or in proximity to the patient 105 in order to gather information to be used for visualization, diagnostics, and therapy (e.g., ablation therapy). This information may be provided to the console system 101 for processing, visualization and operator control and direction, some of which is described below.

The series of leads 110 and intracardiac leads 107 connect electrodes 112 on the surface of the skin of the patient 105 and electrodes 116 on the catheter 120 inside the heart 126, respectively, to the main console 101 of the electrocardiograph device 100. In an example, intracardiac catheter 120 may be used for diagnostic and/or therapeutic treatment, such as for mapping electrical potentials in the heart 126 of the patient 105. In an example, the catheter 120 may be inserted into the vascular system of the patient 105 so that the distal end 114 of the catheter 120 enters a chamber of the patient's heart 126. Although FIG. 1 shows a single catheter 120 and intracardiac lead 107, additional catheters and leads, not shown, with one or more electrodes, transformers and/or sensors may be similarly used. Moreover, an electrocardiograph device 100 may use only surface electrodes 112, or only intracardiac electrodes 116, or both the surface electrodes 112 and intracardiac electrodes 116 for the EKG readings.

A raw EKG signal 115 (i.e., analog input signal) is acquired from the electrodes 112 and/or 116 and converted from an analog to a digital format by the adjustable gain ADC 125. The ADC 125 generates and provides a digital output 117 of the EKG signal 115 by sampling the analog input signal 115 at a sampling rate. The resolution of the ADC 125 indicates the number of discrete values that the ADC 125 can produce over the range of analog values, and can be defined electrically in volts. The number of voltage intervals that the ADC 125 can produce is given by $2^M$, where M is the ADC's resolution in bits.

In an example, the ADC 125 may be implemented as an application specific integrated circuit (ASIC) with 24 bits of resolution, a dynamic range of 0 V to 5 V, and an adjustable gain. Then, the ADC 125 has a maximum voltage resolution defined over the 5 V range of $5V/2^{24}$=0.30 μV. If an input signal is greater than 5 V, (e.g., 6 V), then it is out of range and cannot be sampled by the ADC 125. Similarly, if an analog input signal (e.g., a sine wave) has an amplitude of only 1 V, but is centered at 6 V DC offset, then the input signal is still out of range and cannot be sampled by the ADC 125. In another example, a meaningful analog EKG signal may have a maximum amplitude fluctuation on the order of 1 mV, but may have a 3 V DC bias. Then, the 24 bit resolution of the ADC 125 is used over the entire 3 V range and therefore cannot be used to provide a finer resolution of the smaller fluctuations.

However, if the transformer 118 is used, then the transformer 118 in the heart eliminates the DC offset of the cardiac electrical signal, so that the captured EKG signal is centered around 0V and the entire 24 bits resolution of the ADC 125 can be used to isolate the control point, which is the area of maximum sensitivity where there is maximum change per unit of voltage due to the cardiac electrical activity. Once the direct current (DC) offset is removed, the analog EKG signal may be amplified to the range of the ADC converter 125 (e.g., to 5 V) so that the entire scale of the resolution of the ADC converter 125 is used. For example, if the range of the ADC 124 is 5 V and the amplitude of the measured EKG signal is 1 mV, then a gain of 500 can be applied to the EKG signal to make use of the entire dynamic range.

Once the analog signal is converted, the ADC 125 communicates the digital EKG signal to the processor 130 to produce the EKG graph and/or perform other EKG analysis. Processor 130 may be coupled to data storage 155, data ports and printers 160, other I/O devices 165, and a visual display device 170, which may be used to display the EKG produced by electrocardiograph device 100. The electrocardiograph device 100 and/or any of the components therein may be powered by one or more energy sources 175.

Data storage 155 is any device that records information. Data storage may provide a storage medium for the signals included within device 100 and a place for calculations of processor 130 to be stored.

Microprocessor 145 may be a computer processor which incorporates the functions of a computer's central processing unit (CPU) on a single integrated circuit (IC), or a few integrated circuits. Microprocessor 145 may be a multipurpose, clock driven, register based, programmable electronic device which accepts digital or binary data as input, processes it according to instructions stored in its memory or data storage 155, and provides results as output. Microprocessor 145 contains both combinational logic and sequential digital logic.

Micro controller 150 may be one or more small computers on a single integrated circuit. Micro controller 150 may contain one or more CPUs along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

DSP 140 may perform digital signal processing to perform a wide variety of signal processing operations. The signals processed in this manner are a sequence of numbers that represent samples of a continuous variable in a domain such as time, space, or frequency. Digital signal processing can involve linear or nonlinear operations. Nonlinear signal processing is closely related to nonlinear system identification and can be implemented in the time, frequency, and spatio-temporal domains. The application of digital computation to signal processing allows for many advantages over analog processing in many applications, such as error detection and correction in transmission as well as data compression. DSP is applicable to both streaming data and static (stored) data.

Figure 2:
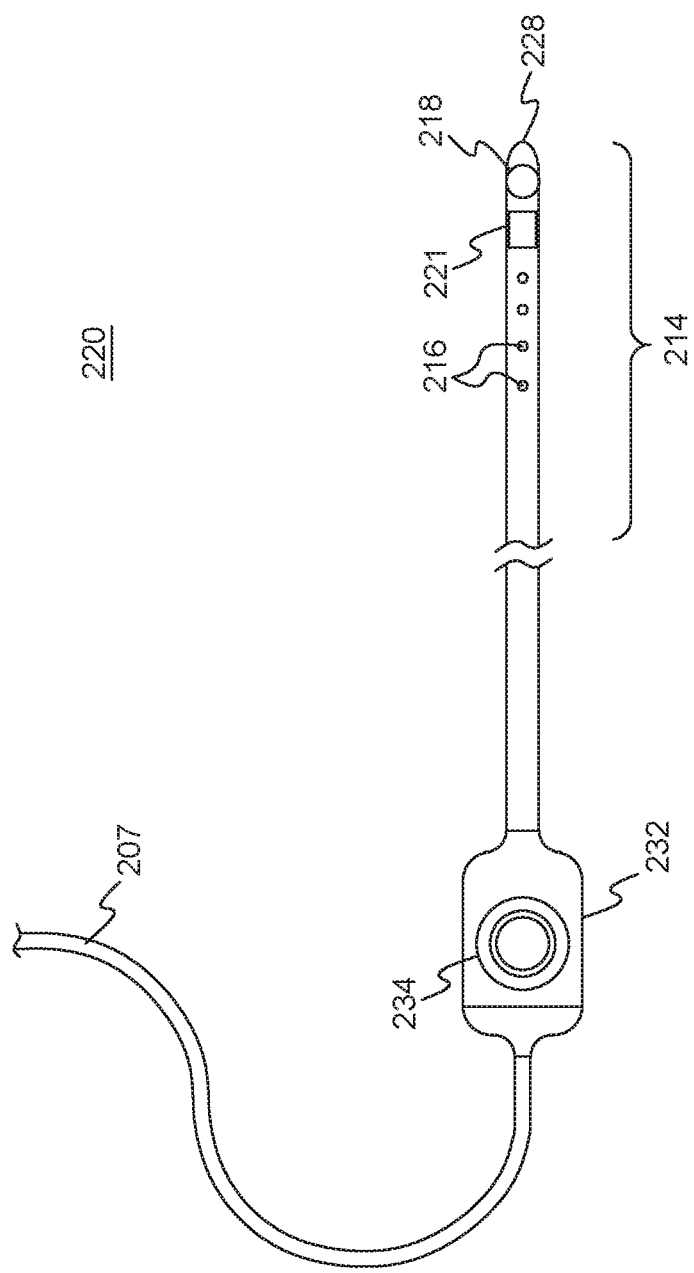
FIG. 2 is a schematic diagram of an example catheter that may be included in the example electrocardiograph device of FIG. 1, in accordance with the disclosures herein.

FIG. 2 is a schematic diagram of an example catheter 220 that may be included in the example electrocardiograph device 100 of FIG. 1 (e.g., catheter 120 in FIG. 1), in accordance with the disclosures herein. The catheter 220 may be connected to an electrocardiograph console via lead 207. The catheter 220 may include, but is not limited to include, any one or more of the following components: distal end 214; electrodes 216; transformer 218; positioning sensors 221; distal tip 228; handle 232; and/or controls 234.

The distal end 214 of the catheter 220 may include electrodes 216 at the distal tip 228 that may be used to measure electrical properties of the cardiac tissue. The electrodes 216 may also be used to send electrical signals to the heart for diagnostic purposes. The electrodes 216 may also perform ablation on defective cardiac tissue by applying energy (e.g., RF energy) directly to the cardiac tissue at the desired location of ablation. In an example, the electrodes 216 may include non-contact electrodes arranged in an array, which may be used to simultaneously receive and measure far-field electrical signals from the walls of the heart chamber of the patient. The electrodes 216 provide information regarding the electrical properties of the heart to an electrocardiograph console for processing.

The distal end 214 includes transformer 218 that may eliminate the DC offset in a captured analog EKG signal, so that the captured EKG signal is centered on 0 V to isolate the control point, which is the area of maximum sensitivity where there is maximum change per unit of voltage due to the cardiac electrical activity.

The distal end 214 may include positioning sensors 221 (also called location sensors) in the distal tip 228 of the catheter 220 that may generate signals used to determine the position and orientation (and/or distance) of the catheter 220 in the body. In an example, the relative position and orientation of the positioning sensors 221, the electrodes 216, and the distal tip 228 are fixed and known in order to facilitate accurate positioning information of the distal tip 228. For example, the position of the positioning sensors 221 may be determined in part based on the relative position to known positions outside the heart (e.g., based on extra-cardiac sensors, not shown). The use of positioning sensors 221 may provide improved location accuracy within the magnetic fields in the surrounding space and provide location information that is adaptable to patient movement because the position information of the catheter 220 is relative to the anatomy of the patient.

The handle 232 of the catheter 220 may be operated by the physician and may include controls 234 to enable the physician to effectively steer the distal tip 228 in the desired direction.

Figure 3:
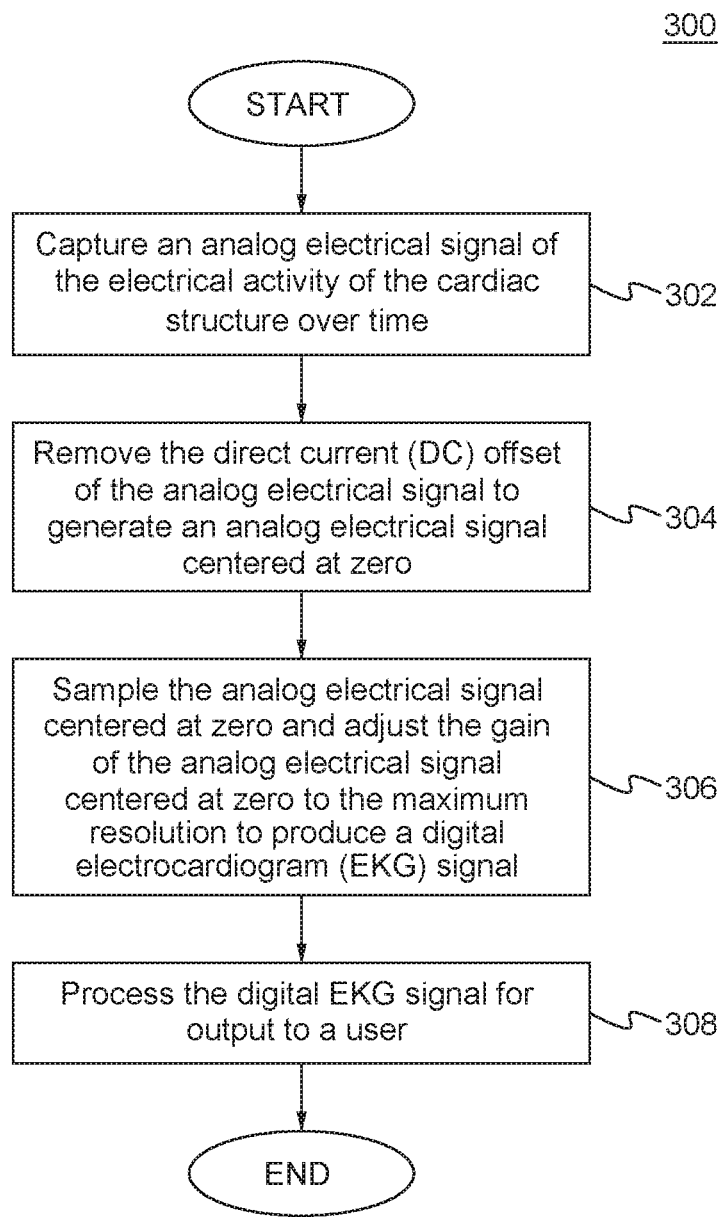
FIG. 3 is a flow diagram of an example procedure for generating an enhanced electrocardiogram (EKG) with single middle point zero reference inside the heart, in accordance with the disclosures herein.

FIG. 3 is a flow diagram of an example procedure 300 for generating an enhanced EKG with single middle point zero reference inside the heart, in accordance with the disclosures herein. The example procedure 300 may be implemented in an electrocardiograph system, such as the example electrocardiograph device 100 of FIG. 1.

At 302, an analog electrical signal of the electrical activity of the cardiac structure over time may be captured, for example using electrodes located on an intracardiac catheter and/or on the surface of the skin. At 304, the DC offset of the analog electrical signal may be removed, for example using an intracardiac transformer, to generate an analog electrical signal centered at zero. At 306, the analog electrical signal centered at zero may be sampled and a gain of the analog electrical signal centered at zero may be adjusted to the maximum range to produce a digital EKG signal. At 308, the digital EKG signal may be processed for output to the user, for example as an EKG reading printed or displayed on a visual display device.

Many variations are possible based on the disclosure herein. Although features and elements are described above in particular combinations, each feature or element can be used alone without the other features and elements or in various combinations with or without other features and elements.

The systems and procedures described herein may be implemented in hardware, and/or software. A computer-based system for performing electrocardiography may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to electrocardiography procedures within the heart, the devices and procedures may be similarly used for electrophysiology procedures in other parts of the body, such as, but not limited to, electroencephalography in the brain, electrooculography in the eye, and electropneumography in the lungs.

The methods provided may include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be mask works that are then used in a semiconductor manufacturing process to manufacture a processor which implements the methods described herein.

The methods or flow charts provided herein may be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system for measuring electrical activity of a cardiac structure, the system comprising:
   a plurality of electrodes positioned in proximity to the cardiac structure and configured to measure an electrical signal of the cardiac structure; and
   a transformer inserted into a chamber of the cardiac structure and configured to emit a low electric charge to remove a direct current (DC) offset of the electrical signal of the cardiac structure.

2. The system of claim 1, wherein the plurality of electrodes include intracardiac electrodes mounted on a catheter configured for insertion into a chamber of the cardiac structure.

3. The system of claim 1, wherein the plurality of electrodes include surface electrodes located on a body surface exterior to the cardiac structure.

4. The system of claim 1, wherein the low electric charge emitted by the transformer is in a range of 1 μV to 100 μV.

5. The system of claim 1, wherein the low electric charge emitted by the transformer isolates an area of maximum sensitivity where there is maximum change per unit of voltage due to cardiac electrical activity.

6. The system of claim 1, wherein the low electric charge emitted by the transformer creates a middle point zero reference point for the plurality of electrodes and removes distortions due to impedance caused by internal body structure.

7. The system of claim 1, further comprising:
   a catheter configured for insertion into a chamber of the cardiac structure, wherein at least a portion of the plurality of electrodes and the transformer are mounted on the catheter; and
   a console system comprising:
      an analog-to-digital converter (ADC) configured to sample the electrical signal with the DC offset removed and adjust a gain of the electrical signal with the DC offset removed to a resolution of the ADC to produce a digital electrocardiogram (EKG) signal; and
      a processor configured to process the digital EKG signal for output to a user.

8. The system of claim 7, wherein the console system further comprises:
   a visual display device configured to visually display the digital EKG signal.

9. The system of claim 7, wherein the resolution of the ADC is based on a dynamic voltage range of the ADC.

10. The system of claim 7, wherein the catheter further comprises:
    positioning sensors configured to generate position and orientation information of the catheter and provide the position and orientation information to the console system.

11. A method for measuring electrical activity of a cardiac structure, the method comprising:
    measuring, by a plurality of electrodes, an electrical signal of the cardiac structure; and
    removing, by a transformer inserted into a chamber of the cardiac structure and configured to emit a low electric charge, a direct current (DC) offset of the electrical signal of the cardiac structure.

12. The method of claim 11, wherein the plurality of electrodes include intracardiac electrodes mounted on a catheter configured for insertion into a chamber of the cardiac structure.

13. The method of claim 11, wherein the plurality of electrodes include surface electrodes located on a body surface exterior to the cardiac structure.

14. The method of claim 11, wherein the low electric charge emitted by the transformer is in a range of 1 μV to 100 μV.

15. The method of claim 11, wherein the low electric charge emitted by the transformer isolates an area of maximum sensitivity where there is maximum change per unit of voltage due to cardiac electrical activity.

16. The method of claim 11, wherein the low electric charge emitted by the transformer creates a middle point zero reference point for the plurality of electrodes and removes distortions due to impedance caused by internal body structure.

17. The method of claim 11, further comprising:
    inserting a catheter into a chamber of the cardiac structure, wherein at least a portion of the plurality of electrodes and the transformer are mounted on the catheter;
    sampling the electrical signal with the DC offset removed and adjusting a gain of the electrical signal with the DC offset removed to produce a digital electrocardiogram (EKG) signal; and
    processing the digital EKG signal for output to a user.

18. The method of claim 17, further comprising:
    visually displaying the digital EKG signal to the user on a visual display device.

19. The method of claim 17, further comprising:
    generating position and orientation information of the catheter.

20. The method of claim 19, further comprising:
    processing and providing the position and orientation information of the catheter to the user.

* * * * *